United States Patent [19]

Georgiev et al.

[11] Patent Number: 4,745,220

[45] Date of Patent: May 17, 1988

[54] SUBSTITUTED ALPHA-(2-TRICYCLO(3.3.1.13,7)-DECYLIDENE)BENZENEACETAMIDE DERIVATIVES

[75] Inventors: Vassil S. Georgiev, Rochester; George B. Mullen, Avon, both of N.Y.

[73] Assignee: Pennwalt Corporation, Philadelphia, Pa.

[21] Appl. No.: 866,840

[22] Filed: May 27, 1986

[51] Int. Cl.$^4$ ............... C07C 103/26; C07C 103/22; A61K 31/165
[52] U.S. Cl. .................................. 564/172; 564/180
[58] Field of Search .................. 564/172, 180, 181; 514/617, 622

[56] References Cited

U.S. PATENT DOCUMENTS 3,624,126  11/1971  Narayanan .................. 260/468 B

OTHER PUBLICATIONS

Fuks et al., Chem. Ber., 103, 564–572 (1970).
Chemical Abstracts 64: 19630h (1966).
Chemical Abstracts 65: 10524d (1966).
Aigami et al., "Biologically Active Polycycloalkanes, 1 Antiviral Adamantane Derivatives", J. Med. Chem. 18, 713–721 (1975).

Primary Examiner—Floyd D. Higel
Assistant Examiner—Carolyn S. Greason

[57]  ABSTRACT

Substituted α-[2'-tricyclo[3.3.1.1$^{3,7}$]decylidene]-benzenacetamide derivatives of the formula:

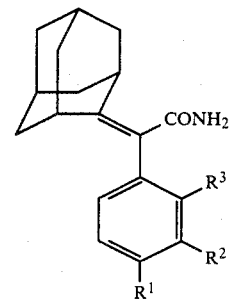

where the $R^1$, $R^2$ and $R^3$ substitutents are independently selected from hydrogen, lower alkyl, lower alkoxy, halogen and trifluoromethyl, provided that at least one of such substitutents is hydrogen, have antihypoxia, antiparkinson, and/or anticonvulsant activities.

10 Claims, No Drawings

SUBSTITUTED ALPHA-(2-TRICYCLO(3.3.1.1³,⁷)-DECYLIDENE)-BENZENEACETAMIDE DERIVATIVES

BACKGROUND OF THE INVENTION

In our concurrently filed application entitled, "Substituted α-[2'-tricyclo[3.3.1.1$^{3,7}$]decylidene]benzeneacetonitrile Derivatives", whose teachings are hereby incorporated by reference, we have described substituted α-[2'-tricyclo[3.3.1.1$^{3,7}$]decylidene]benzeneacetonitrile derivatives which have antihypoxia and anti-inflammatory activities. We have now prepared the related benzeneacetamide derivatives which possess antihypoxia, antiparkinson and/or anticonvulsant activities, that is they either protect warm-blooded animals from the effects of oxygen deprivation, reduce pentylenetetrazole- or electric shock-induced seizures or reduce N-carbamoyl-2-(2,6-dichlorophenyl)acetamide hydrochloride-induced tremors.

BRIEF SUMMARY OF THE INVENTION

In accordance with this invention, there are provided substituted α-[2'-tricyclo[3.3.1.1$^{3,7}$]decylidene]benzeneacetamide derivatives of the formula:

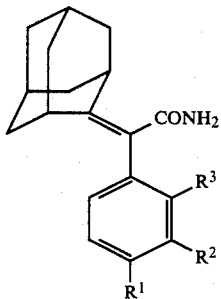

where the $R^1$, $R^2$ and $R^3$ substituents are independently selected from hydrogen, lower alkyl, lower alkoxy, halogen and trifluoromethyl, provided that at least one of such substituents is hydrogen.

DETAILED DESCRIPTION

As used herein the terms "lower alkyl" and "lower alkoxy" refer to straight and branched chain alkylene groups having 1 to 4 carbons and "halogen" refers to chlorine, bromine, iodine and fluorine (preferably chlorine).

As described in the following Examples, the compounds of the invention can be prepared by alkaline hydrolysis from the corresponding α-[2'-tricyclo[3.3.1.1$^{3,7}$]decylidene]benzeneacetonitrile derivatives 3 which are described in our copending application and which can be obtained by the condensation of 2-adamantanone 1 with the appropriate phenylacetonitrile 2 in tetrahydrofuran solution and in the presence of potassium tert-butoxide. The reaction scheme is as follows:

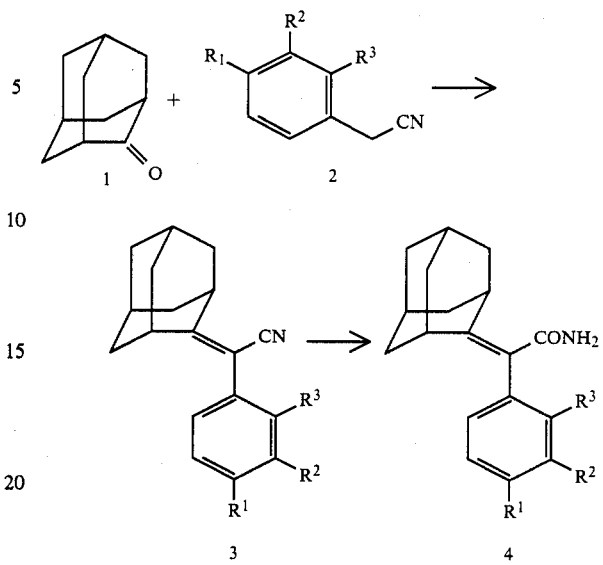

EXAMPLE 1

4-Methyl-α-[2'-tricyclo[3.3.1.1$^{3,7}$]decylidene]benzeneacetamide

Powdered potassium hydroxide (61.1 g, 1.10 mol) was added to a solution of 30.18 g (0.115 mol) 4-methyl-α-[2'-tricyclo[3.3.1.1$^{3,7}$]decylidene]benzeneacetonitrile (3, $R^1$=CH$_3$, $R^2$=$R^3$=H) in 300 ml tert-butyl alcohol. The resulting suspension was refluxed for 20 hours, then cooled to room temperature, poured onto ice-water, and extracted with chloroform. The organic layer was washed sequentially with water and saturated aqueous solution of sodium chloride, dried over magnesium sulfate and the solvent evaporated in vacuo. 16.40 g (51%) of product compound (4, $R^1$=CH$_3$, $R^2$=$R^3$=H) was obtained after recrystallization from methanol, m.p. 167°-170° C. Anal. Calcd. for C$_{19}$H$_{23}$NO: C, 81.10; H, 8.24; N, 4.98. Found: C, 80.64; H, 8.30; N, 5.02.

The compounds of Examples 2-9 below are prepared according to the process of Example 1 by reacting the appropriate benzeneacetonitrile with potassium hydroxide in approximately the same molar proportions.

EXAMPLE 2

α-[2'-Tricyclo[3.3.1.1$^{3,7}$]decylidene]benzeneacetamide

The title compound (4, $R^1$=$R^2$=$R^3$=H) was prepared by a method similar to that described in Example 1 by reacting α-[2'-tricyclo[3.3.1.1$^{3,7}$]decylidene]benzeneacetonitrile (3, $R^1$=$R^2$=$R^3$=H) with powdered potassium hydroxide. The product has a melting point of 147°-148° C. (ethyl acetate). Anal. Calcd. for C$_{18}$H$_{21}$NO: C, 80.86; H, 7.92; N, 5.24, Found: C, 80.99; H, 8.03; N, 5.12.

EXAMPLE 3

4-Chloro-α-[2'-tricyclo[3.3.1.1$^{3,7}$]decylidene]benzeneacetamide

The title compound (4, $R^1$=Cl, $R^2$=$R^3$=H) was prepared by a method similar to that described in Example 1 by reacting 4-chloro-α-[2'-tricyclo[3.3.1.1$^{3,7}$]decylidene]benzeneacetonitrile (3, $R^1$=Cl, $R^2$=$R^3$=H) with powdered potassium hydroxide. The product has a melting point of 179°-183° C. (ethanol).

Anal. Calcd. for $C_{18}H_{20}ClNO$: C, 71.63; H, 6.68; N, 4.64; Cl, 11.75. Found: C, 72.04; H, 6.80; N, 4.62; Cl, 11.94.

EXAMPLE 4

2,4-Dichloro-α-[2'-tricyclo[3.3.1.1$^{3,7}$]decylidene]benzeneacetamide

The title compound (4, $R^1=R^3=Cl$, $R^2=H$) was prepared by a method similar to that described in Example 1 by reacting 2,4-dichloro-α-[2'-tricyclo[3.3.1.1$^{3,7}$]decylidene]benzeneacetonitrile (3, $R^1=R^3=Cl$, $R^2=H$) with powdered potassium hydroxide. The product has a melting point of 178°–180° C. (ethanol). Anal. Calcd. for $C_{18}H_{19}Cl_2NO$: C, 64.29; H, 5.70; N, 4.17; Cl, 21.09. Found: C, 64.44; H, 5.83; N, 4.10; Cl, 20.72.

EXAMPLE 5

3-Methyl-α-[2'-tricyclo[3.3.1.1$^{3,7}$]decylidene]benzeneacetamide

The title compound (4, $R^1=R^3=H$, $R^2=CH_3$) was prepared by a method similar to that described in Example 1 by reacting 3-methyl-α-[2'-tricyclo[3.3.1.1$^{3,7}$]decylidene]benzeneacetonitrile (3, $R^1=R^3=H$, $R^2=CH_3$) with powdered potassium hydroxide. The product has a melting point of 67°–70° C. (ether). Anal. Calcd. for $C_{19}H_{23}NO$: C, 80.10; H, 8.24; N, 4.98. Found: C, 80.43; H, 8.50; N, 4.78.

EXAMPLE 6

3-Chloro-α-[2'-tricyclo[3.3.1.1$^{3,7}$]decylidene]benzeneacetamide

The title compound (4, $R^1=R^3=H$, $R^2=Cl$) was prepared by a method similar to that described in Example 1 by reacting 3-chloro-α-[2'-tricyclo[3.3.1.1$^{3,7}$]decylidene]benzeneacetonitrile (3, $R^1=R^3=H$, $R^2=Cl$) with powdered potassium hydroxide. The product has a melting point of 140°–143° C. (ether). Anal. Calcd. for $C_{18}H_{20}ClNO$: C, 71.63; H, 6.68; N, 4.64; Cl, 11.75. Found: C, 71.71; H, 6.90; N, 4.68; Cl, 11.78.

EXAMPLE 7

3-Trifluoromethyl-α-[2'-tricyclo[3.3.1.1$^{3,7}$]decylidene]-benzeneacetamide

The title compound (4, $R^1=R^3=H$, $R^2=CF_3$) was prepared by a method similar to that described in Example 1 by reacting 3-trifluoromethyl-α-[2'-tricyclo[3.3.1.1$^{3,7}$]decylidene]benzeneacetonitrile (3, $R^1=R^3=H$, $R^2=CF_3$] with powdered potassium hydroxide. The product has a melting point of 149°–151° C. (ethyl acetate). Anal. Calcd. for $C_{19}H_{20}F_3NO$: C, 68.05; H, 6.01; N, 4.18; F, 17.00. Found: C, 68.38; H, 6.07; N, 4.19; F, 17.23.

EXAMPLE 8

2-Methyl-α-[2'-tricyclo[3.3.1.1$^{3,7}$]decylidene]-benzeneacetamide

The title compound (4, $R^1=R^2=H$, $R^3=CH_3$) was prepared by a method similar to that described in Example 1 by reacting 2-methyl-α-[2'-tricyclo[3.3.1.1$^{3,7}$]decylidene]benzeneacetonitrile (3, $R^1=R^2=H$, $R^3=CH_3$) with powdered potassium hydroxide. The product has a melting point of 159°–162° C. (ethyl acetate). Anal. Calcd. for $C_{19}H_{23}NO$: C, 81.10; H, 8.24; N, 4.98. Found: C, 81.34; H, 8.59; N, 4.85.

EXAMPLE 9

2-Methoxy-α-[2'-tricyclo[3.3.1.1$^{3,7}$]decylidene]benzeneacetamide

The title compound (4, $R^1=R^2=H$, $R^3=OCH_3$) was prepared by a method similar to that described in Example 1 by reacting 2-methoxy-α-[2'-tricyclo[3.3.1.1$^{3,7}$]decylidene]benzeneacetonitrile (3, $R^1=R^3=H$, $R^3=OCH_3$) with powdered potassium hydroxide. The product has a melting point of 155°–157° C. (ethyl acetate). Anal. Calcd. for $C_{19}H_{23}NO_2$: C, 76.74; H, 7.79; N, 4.71. Found: C, 76.63; H, 7.97; N, 4.38.

Compounds possessing useful antihypoxia activity extend the lifetime of animals exposed to a hypoxic environment. This activity is conveniently measured in mice. Groups of mice are tested at various times after the intraperitoneal administration of the test compound dissolved in saline in dosages of 1 to 100 mk/kg of mouse weight. The animals' survival time in a hypoxic environment (96% nitrogen and 4% oxygen) is recorded. A statistical comparison (Wilcoxon Rank sum) is made between coincident vehicle treated animals and the experimental group. The compounds of Examples 1, 3, 4 and 6 to 9 were tested at the 100 mg/kg dosage level and were found active.

The evaluation of the anti-convulsant activity of drugs is based mainly on their ability to block pentylenetetrazole (PTZ)- and/or electric shock-induced convulsions. In general, compounds which protect animals against pentylenetetrazole-induced seizures are useful in the treatment of petit mal epilepsy, and drugs which protect animals against electrically induced convulsions are effective in the treatment of grand mal and focal seizures. Compounds possessing broader activity which protect animals against both forms of induced seizures may be useful in the treatment of adult petit mal and psychomotor epilepsies.

In the PTZ-induced seizure test two groups of 5 mice each are administered the test compound at ¼ of the LD50 or vehicle intraperitoneally (i.p.). Thirty minutes later each mouse is administered PTZ, 150 mg/kg i.p. The mice are housed by groups in plastic cages. The animals are observed for 15 minutes immediately following PTZ administration. Alteration of the convulsive pattern such as delayed onset of convulsions, changes in the type of convulsions and prevention of convulsions are noted. The number of survivors 15 minutes after PTZ administration is recorded.

The dose of PTZ used as a convulsive challenge is higher than the LD 100 dose, therefore, the number of surviving mice 15 minutes post PTZ can be used as an index of anticonvulsive activity. Active compounds are considered as those that protect 3 or more mice. Most compounds which afford protection against death also delay and moderate or prevent PTZ-induced seizures. The seizure pattern of untreated mice (controls) is: (1) initial twitching, (2) a more severe generalized jerking of the body usually accompanied by a squeak which is followed immediately by (3) frank clonic convulsion which lead to tonic convulsions with tonic extension of the hind limbs. The compounds of Examples 2 and 6 were found active at a dosage of 400 mg/kg of mouse weight.

In the electric shock test, mice are subjected to a shock of 50 mA for 0.2 seconds applied through saline-wetted corneal electrodes. The control group is tested similarly. Untreated mice subjected to electric shock exhibit a typical seizure pattern. Tonic flexion occurs immediately after shock. This changes to tonic extension (hind limb) within 0.5 to 2 seconds and then into generalized clonic convulsions followed by depression and recovery. The criterion for drug activity is prevention of hind limb tonic extension in 3 or more mice. Some compounds will prevent the tonic phase of the seizure entirely (flexion and extension). The compounds of Examples 2 and 5 were found to be active at a dosage of 400 mg/kg of mouse weight.

We claim:

1. A compound of the formula:

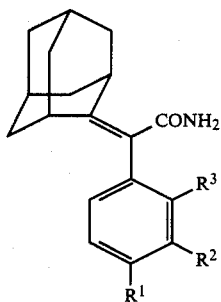

where the $R^1$, $R^2$ and $R^3$ substituents are independently selected from hydrogen, lower alkyl, lower alkoxy, halogen, and trifluoromethyl provided that at least one of such substituents is hydrogen.

2. A compound according to claim 1 wherein the compound is 4-methyl-α-[2'-tricyclo[3.3.1.1$^{3,7}$]decylidene]benezeneacetamide.

3. A compound according to claim 1 wherein the compound is α-[2'-tricyclo[3.3.1.1$^{3,7}$]decylidene]benzeneacetamide.

4. A compound according to claim 1 wherein the compound is 4-chloro-α-[2'-tricyclo[3.3.1.1$^{3,7}$]decylidene]benzeneacetamide.

5. A compound according to claim 1 wherein the compound is 2,4-dichloro-α-[2'-tricyclo[3.3.1.1$^{3,7}$]decylidene]benzeneacetamide.

6. A compound according to claim 1 wherein the compound is 3-methyl-α-[2'-tricyclo[3.3.1.1$^{3,7}$]decylidene]benzeneacetamide.

7. A compound according to claim 1 wherein the compound is 3-chloro-α-[2'-tricyclo[3.3.1.1$^{3,7}$]decylidene]benzeneacetamide.

8. A compound according to claim 1 wherein the compound is 3-trifluoromethyl-α-[2'-tricyclo[3.3.1.1$^{3,7}$]decylidene]benzeneacetamide.

9. A compound according to claim 1 wherein the compound is 2-methyl-α-[2'-tricyclo[3.3.1.1$^{3,7}$]decylidene]benzeneacetamide.

10. A compound according to claim 1 wherein the compound is 2-methoxy-α-[2'-tricyclo[3.3.1.1$^{3,7}$]decylidene]benzeneacetamide.

* * * * *